(12) United States Patent
Chou et al.

(10) Patent No.: US 12,239,478 B2
(45) Date of Patent: Mar. 4, 2025

(54) WEARABLE HEART SOUND DETECTION SYSTEM AND METHOD THEREOF

(71) Applicant: Decentralized Biotechnology Intelligence Co., Ltd., Taipei (TW)

(72) Inventors: Yao-Sheng Chou, Taipei (TW); Wei-Sheng Su, Taipei (TW); Hsiao-Yi Lin, Taipei (TW)

(73) Assignee: Decentralized Biotechnology Intelligence Co., Ltd., Taipei (TW)

( * ) Notice: Subject to any disclaimer, the term of this patent is extended or adjusted under 35 U.S.C. 154(b) by 256 days.

(21) Appl. No.: 17/966,831

(22) Filed: Oct. 15, 2022

(65) Prior Publication Data
US 2023/0309949 A1    Oct. 5, 2023

(30) Foreign Application Priority Data

Apr. 1, 2022    (TW) .................................. 111112848

(51) Int. Cl.
*A61B 7/04*        (2006.01)
*A61B 5/00*        (2006.01)
(Continued)

(52) U.S. Cl.
CPC ............ *A61B 7/04* (2013.01); *A61B 5/02427* (2013.01); *A61B 5/02438* (2013.01);
(Continued)

(58) Field of Classification Search
None
See application file for complete search history.

(56) References Cited

U.S. PATENT DOCUMENTS

2010/0234706 A1* 9/2010 Gilland .............. A61B 5/14552
                                                    600/344
2012/0265080 A1* 10/2012 Yu ........................ A61B 5/6893
                                                    600/509
(Continued)

FOREIGN PATENT DOCUMENTS

CA            3021919 C  *  8/2019  ......... A61B 5/02438
WO    WO-2016154425 A1  *  9/2016  ........... A61B 5/1118

OTHER PUBLICATIONS

Cepeda et al., "Heart Rate Detection using a Piezoelectric Ceramic Sensor: Preliminary results". pp. 1-8. 2022. (Year: 2022).*
(Continued)

*Primary Examiner* — Qin Zhu
(74) *Attorney, Agent, or Firm* — Chih Feng Yeh; Yongjean Consulting Inc.

(57) ABSTRACT

A wearable heart sound detection system, which includes an acoustic sensing device for collecting heart sound signals of the body, performing signal amplification, filtering, digitization and other preprocessing on the collected heart sound signals, and outputting the preprocessed heart sound signals; a computing electronic device communicatively coupled to the acoustic sensing device for acquiring the preprocessed heart sound signal, and a cloud data database communicatively coupled to the external computing electronic device. The acoustic device includes a capacitive sound sensor, a piezoelectric sound sensor and a circuit assembly. The circuit assembly is respectively electrically connected with the capacitive sound sensor and the piezoelectric sound sensor. The circuit assembly, the capacitive sound sensor and the piezoelectric sound sensor are integrated on a flexible substrate.

18 Claims, 9 Drawing Sheets

(51) Int. Cl.
  *A61B 5/024* (2006.01)
  *A61B 5/117* (2016.01)
  *A61B 7/02* (2006.01)
  *H04R 1/04* (2006.01)
  *H04R 3/00* (2006.01)
  *H04R 17/02* (2006.01)
  *H04R 19/04* (2006.01)
  *H04R 23/02* (2006.01)

(52) U.S. Cl.
  CPC ............ *A61B 5/117* (2013.01); *A61B 5/7225* (2013.01); *A61B 5/7257* (2013.01); *A61B 5/7267* (2013.01); *A61B 5/7275* (2013.01); *A61B 5/746* (2013.01)

(56) References Cited

U.S. PATENT DOCUMENTS

2015/0011851 A1* 1/2015 Mehta ................ A61B 5/02433
　　　　　　　　　　　　　　　　　　　　　600/324
2020/0029840 A1* 1/2020 Nguyen ................ G16H 40/67

OTHER PUBLICATIONS

Goroso et al., "Monitoring heart rate variability on-line used mobile telephone 3G e-health service oriented" pp. 1-10. 2013. (Year: 2013).*

* cited by examiner

WEARABLE HEART SOUND DETECTION SYSTEM AND METHOD THEREOF

CROSS-REFERENCE STATEMENT

The present application is based on, and claims priority from, Taiwan Patent Application Serial Number 111112848, filed Apr. 1, 2022, the disclosure of which is hereby incorporated by reference herein in its entirety.

BACKGROUND

1. Technical Field

The present invention relates to technical field of medical equipments, and more particularly, a wearable heart sound detection system and a method thereof.

2. Related Art

With the rapid development of microcomputer, microelectronic, wireless communication, weak signal detection technologies and material science, a wearable health detection system integrating various small sensors, wireless transmitter-receiver modules and control processing units has become one of the key research and development projects by researchers.

Heart sound detection equipment, such as a stethoscope, is a medical instrument for detecting sounds produced by organs in the body. An electronic stethoscope collects the sounds of the heart and lungs and other organ activities by placing the earpiece in the corresponding part of the organism under test, and interprets these sounds. These sounds are converted into electrical signals, and after amplification these signals, which can be directly emitted by the speaker, so that doctors or related personnel can determine the cause or lesion according to the corresponding sound signals and make a correct diagnosis.

In the heartbeat cycle, the mechanical vibrations caused by factors such as myocardial contraction, valve opening and closing, blood acceleration and deceleration on the cardiovascular pressurization and decompression, as well as the eddy current of the stroke, which can be transmitted to the chest wall through the surrounding tissues. When placed the detection device on certain areas of the chest wall, sounds called heart sounds can be heard. Certain abnormal heart activities can produce murmurs or other abnormal heart sounds. Therefore, listening to heart sounds or recording phonocardiogram (PCG) can effectively remedy for the deficiencies of cardiac auscultation.

Heart failure is a prevalent public health problem worldwide, which poses a huge burden on overall healthcare costs. In recent years, as people pay more attention to their own health, health management methods that monitor their physical and mental states in daily basis have became more popular by recording and analyzing people's physiological information for a long time ranging from several hours to several months.

In terms of obtaining people's physiological information, which may include heartbeat rate or R-R intervals, ECG waveform, number of steps, physical activities, body acceleration, etc. By monitoring these physiological information in daily life, which can be effectively used to improve people's health, or to detect the diseases at early stage, etc.

With the aging of the population, medical care products for health warning and care have become the current development trend. In order to detect symptoms at early stage, especially cardiac diseases with a very high sudden death rate, the wearable heart sound device can provide a real-time and effective detection and recording for abnormal heartbeat signals. Doctors can analyze these real-time recorded physiological audio signals and provide health warning and care solutions.

For the aforementioned purposes, a novel wearable heart sound detection system and a corresponding method are needed, so that it can be applied to situations such as home care, ambulatory care, occupational safety and health management, and autonomous health warning.

SUMMARY

Based on the above descriptions, in one aspect of the present invention, a heart sound detection system to solve the deficiencies of the prior art. The wearable heart sound detection system includes an acoustic sensing device for collecting heart sound signals of the body, performing signal amplification, filtering, digitization and other preprocessing on the collected heart sound signals, and outputting the preprocessed heart sound signals; a computing electronic device communicatively coupled to the acoustic sensing device for acquiring the preprocessed heart sound signal, and a cloud data database communicatively coupled to the external computing electronic device. The acoustic device includes a capacitive sound sensor, a piezoelectric sound sensor and a circuit assembly. The circuit assembly is respectively electrically connected with the capacitive sound sensor and the piezoelectric sound sensor. The circuit assembly, the capacitive sound sensor and the piezoelectric sound sensor are mounted on a flexible substrate.

In one preferred embodiment, the circuit assembly at least includes a plurality of amplifiers, a plurality of filters, a plurality of analog-to-digital converters, a microprocessor, a storage device, a wireless transmission device; output end of the capacitive sound sensor electrically connected to a first amplifier of the plurality of amplifiers, the first amplifier electrically connected to a first filter of the plurality of filters, the first filter electrically connected to a first analog-to-digital converter of the plurality of analog-to-digital converters, and the first analog-to-digital converter electrically connected to the microprocessor, wherein the first analog-to-digital converter outputs amplified, filtered and digitized first heart sound signals; output end of the piezoelectric sound sensor electrically connected to a second amplifier of the plurality of amplifiers, the second amplifier electrically connected to a second filter of the plurality of filters, the second filter electrically connected to a second analog-to-digital converter of the plurality of analog-to-digital converters, and the second analog-to-digital converter electrically connected to the microprocessor, wherein the second analog-to-digital converter outputs amplified, filtered and digitized second heart sound signals; the microprocessor receiving and processing the digitized first heart sound signals and the digitized second heart sound signals to obtain de-noising and stable preprocessed first heart sound signals and preprocessed second heart sound signals. Where the microprocessor execute instructions to store the preprocessed first heart sound signals and the preprocessed second heart sound signals in the storage device electrically connected to the microprocessor, or to send the preprocessed first heart sound signals and the preprocessed second heart sound signals to the external computing electronic device via the wireless transmission device for further analysis.

In one preferred embodiment, the circuit assembly, the capacitive sound sensor and the piezoelectric sound sensor are arranged as follows: the capacitive sound sensor been disposed on a surface of the circuit assembly; a soundproof ring been arranged on the surface and enclosed to encapsulate the capacitive sound sensor and the circuit assembly to form a resonant cavity; the piezoelectric sound sensor been disposed on a side of the soundproof ring not in contact with the circuit assembly, wherein the piezoelectric sound sensor is attached to the user's skin near heart.

In one preferred embodiment, the piezoelectric sound sensor is further provided with a plurality of through holes, enabling that the heart sound signals can enter the resonant cavity of the capacitive sound sensor through the plurality of through holes.

In one preferred embodiment, the piezoelectric sound sensor is acted as a diaphragm to improve low-frequency sound signal response of the capacitive sound sensor.

In one preferred embodiment, the flexible substrate is made of polyimide (PI), polyethylene terephthalate (PET), or textile.

In one preferred embodiment, the wearable heart sound detection system further includes following steps to establish the system: providing an acoustic sensing device for collecting heart sound signals of user's body and outputting preprocessed heart sound signals; providing an external computing electronic device communicatively coupled to the acoustic sensing device for acquiring the preprocessed heart sound signals; and providing a cloud database communicatively coupled to the external computing electronic device; establishing attachment confirmation between the user's body and the acoustic sensing device; collecting the user's biometric features; identifying the user's identity by the collected biometric features; capturing the user's heartbeat signals including heart sound signals by the acoustic sensing device; filtering and amplifying the heart sound signals; performing heart rhythm analysis on the heart sound signals by the acoustic sensing device; checking whether emergency situations existed after the heart rhythm analysis being performed; sending out alarms by the external computing electronic device, if one of the emergency situations is justified, otherwise sending out the heart sound signals to the external computing electronic device for detailed signal processing and continuously capturing the user's heartbeat signals; extracting feature points of the heart sound signals by the external computing electronic device; performing artificial intelligence (AI) comparison and status classification between the extracted feature points and with previous stored data provided by the cloud database; archiving results of the AI comparison and status classification on the cloud database as references for subsequent comparisons and offering the results to interpret and provide medical-related advices by medical specialists.

In one preferred embodiment, the speaker coupled to the frame body is disposed inside a cavity interconnected with the frame body.

In one preferred embodiment, the AI comparison and the status classification are performed by an AI algorithm installed on the external computing electronic device to preliminarily classify normal heart sound signals and abnormal heart sound signals.

In one preferred embodiment, the AI algorithm includes performing steps of pre-filtering and normalizing the heart sound signals been input; extracting time-domain and frequency-domain features of the heart sound signals been input; outputting classification results by adopting a convolutional neural networks (CNN) model.

In one preferred embodiment, the detailed signal processing includes performing filtering, wavelet analysis, and Fourier transform over the heart sound signals.

In one preferred embodiment, size of the plurality of through holes is ranging between 10 μm-1000 μm.

In one preferred embodiment, the acoustic sensing device is capable of collecting the heart sound signals of the user's body while been disposed within a distance without need to contact with the user's body.

In one preferred embodiment, the distance is ranging between 0 cm-5 cm.

BRIEF DESCRIPTION OF THE DRAWINGS

The components, characteristics and advantages of the present invention may be understood by the detailed descriptions of the preferred embodiments outlined in the specification and the drawings attached.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

The present invention proposes a wearable heart sound detection system, which mainly utilizes a wearable heart sound detection device combined with a sound sensing device and wireless transmission to act as a portable heart sound collection device. The wearable heart sound detection system can be connected with the internet of things (IoT). The collected physiological data (for example, personal heart sounds) are processed by a handheld electronic computing device (mobile device) and then stored in a cloud server via a cloud network.

Figure 1:
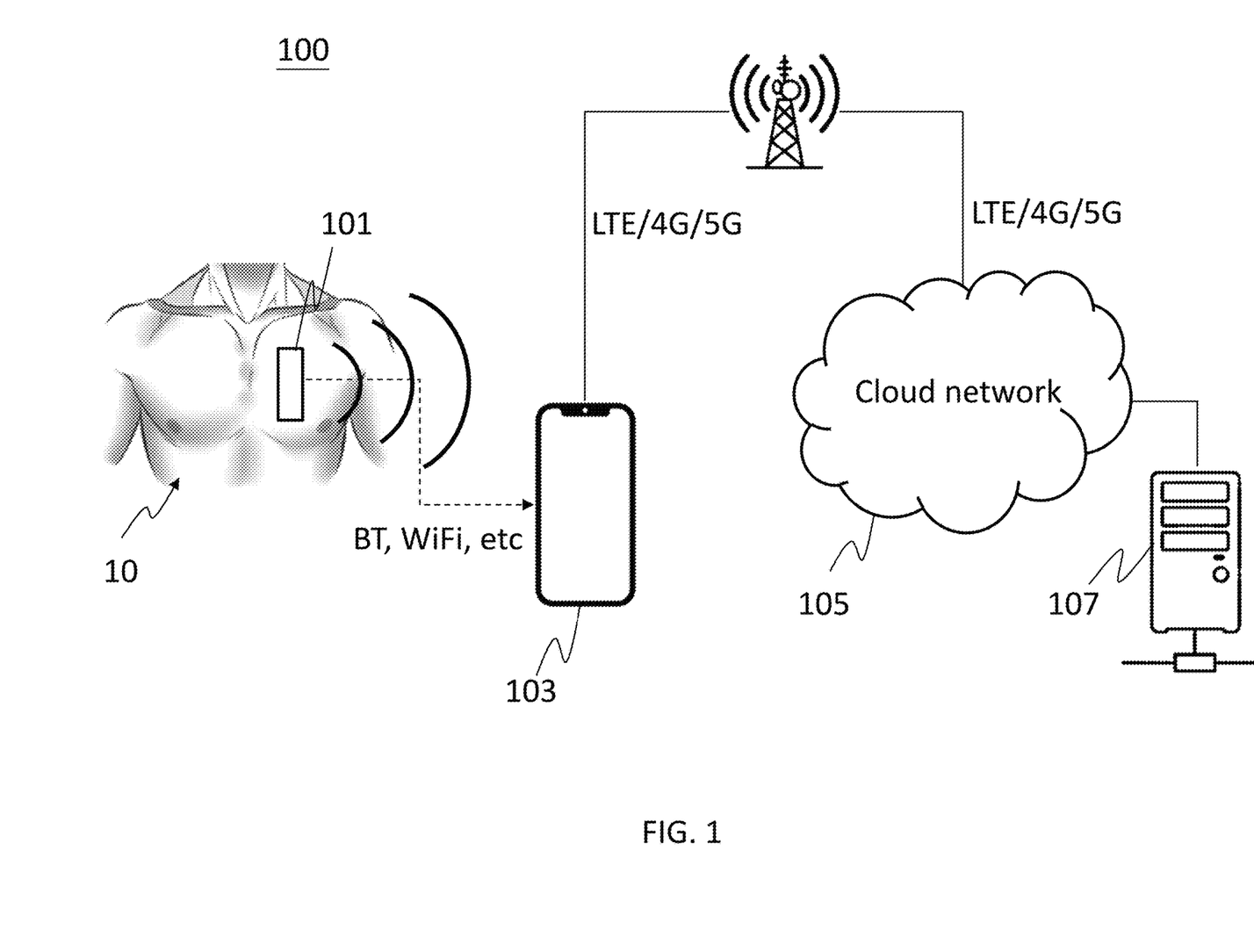
FIG. 1 illustrates the system architecture proposed by the present invention.

FIG. 1 shows a wearable heart sound detection system 100, which having main structure includes a heart sound capturing device 101 been attached to the user 10 in form of a monitoring patch. The heart sound capturing device 101 can communicatively connected to a mobile device (e.g., an external computing electronic device such as a smart phone or tablet computer) 103. The heart sound data collected by the wearable heart sound capturing device 101 can be uploaded to the cloud server 107 from the mobile device 103 via the cloud network 105 through wireless transmission (e.g., wireless communication such as Bluetooth or WiFi). In the cloud server 107, the collected data will be stored in the cloud database. The wearable heart sound detection system 100 also includes at least one application program installed in the mobile device, the application program including instructions for receiving and sending data between the wearable heart sound capturing device 101, the mobile device 103 and the cloud server 105. The above-mentioned application program can be operated based on platform, such as Android, Windows 10 or iOS operating system, and can upload the collected data/signals, such as heart sound signals and their waveforms, to the cloud server 105 for storage, and can also be used to analyze and characterize the data for generating evaluation report and then providing medical advice accordingly through extraction and data analysis algorithms.

The heart sound capturing device 101 can be attached to the chest of the user 10 in form of monitoring patch, which can sense the sound signals of human's body through built-in acoustic sensors. The acoustic sensors are mainly piezoelectric sensor and microphone, where the piezoelectric sensor is mainly composed of a piezoelectric material layer (for example, polyvinylidene fluoride (PVDF) polymer piezoelectric film, lead zirconate titanate (PZT), or other materials have similar properties), and its upper and lower surfaces are plated with conductive metals (for example, aluminum (Al), copper (Cu), etc.). The upper and lower layers of metal are individually connect to the circuit board with a lead, which can be used to measure the voltage signals generated by vibrations. The main composition of the microphone is a conventional capacitive sensor, which uses an ultra-thin material as the diaphragm (for example, 30 μm thick glass), plated with conductive material, and encapsulates the diaphragm with a circuit board by means of sealant to form a resonance chamber. The purpose of forming the resonant chamber is to use the sounds emitted by the heartbeats to vibrate the diaphragm, so that corresponding capacitance changes can occur between the diaphragm and the circuit board. Therefore, the heart sound capturing device captures these capacitance changes to record the heartbeats.

Figures 2A, 2B:
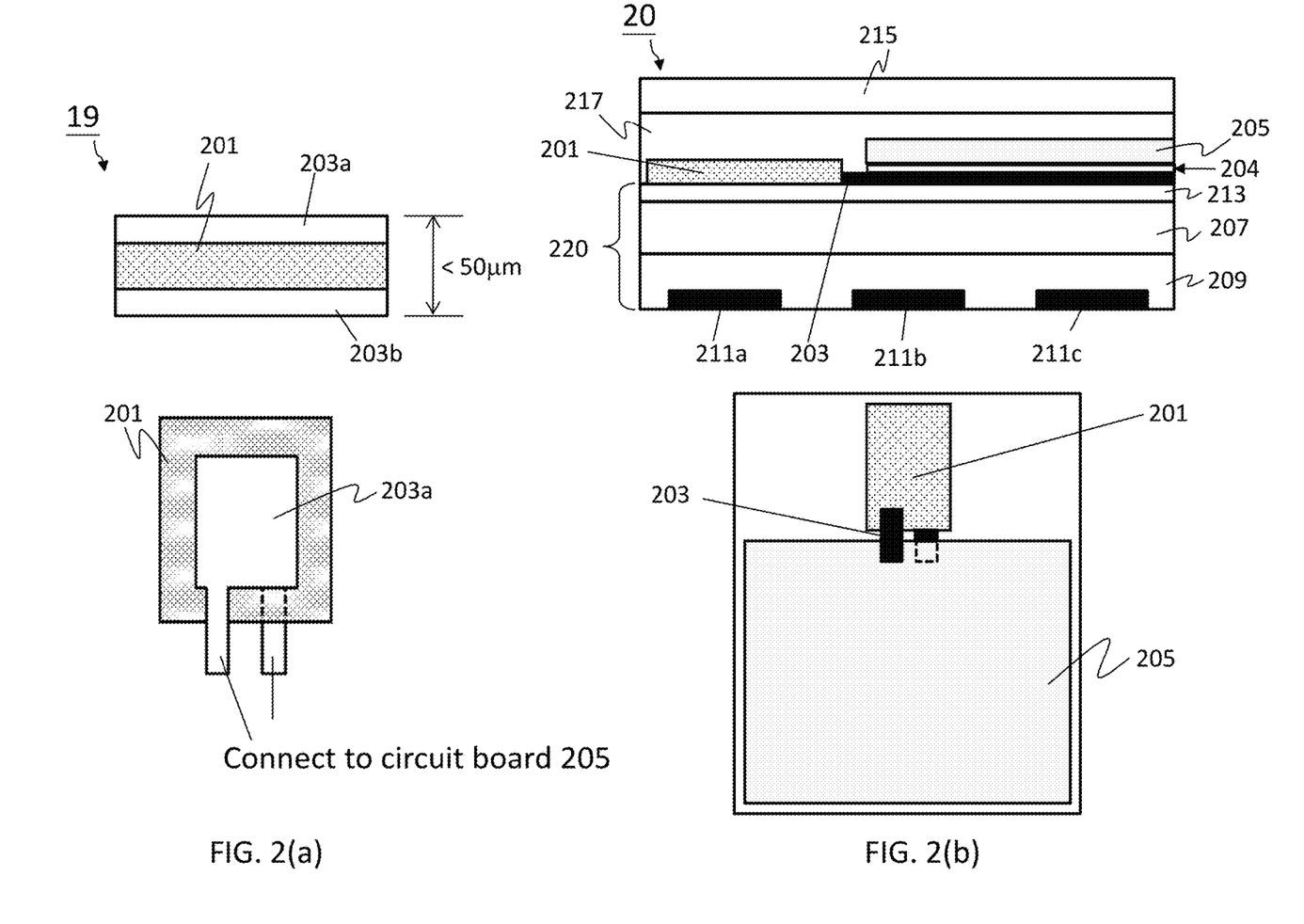
FIG. 2(a) illustrates the side view showing the structure of the piezoelectric sensor according to one embodiment of the present invention.
FIG. 2(b) illustrates the proposed piezoelectric patch structure according to one embodiment of the present invention.

FIG. 2(a) illustrates the side view showing the structure of the piezoelectric sensor 19 according to one embodiment of the present invention. The top of the figure shows that the piezoelectric sensor is mainly composed of a piezoelectric material layer (for example, polyvinylidene fluoride (PVDF) polymer piezoelectric film, lead zirconate titanate (PZT) and other materials) 201, the upper and lower surfaces of which are plating with conductive metal (e.g., aluminum (Al), or copper (Cu), etc.). The bottom of the figure shows a top view of the piezoelectric sensor structure 19, wherein the upper and lower metal electrodes (203a, 203b) are respectively connect to the circuit board 205 by a lead, which can be used to measure the voltage signals generated by vibrations.

In one embodiment, the thickness of the piezoelectric sensor is less than 50 μm.

FIG. 2(b) illustrates the proposed piezoelectric patch structure 20 according to one embodiment of the present invention. The top of the figure is a side view of the piezoelectric patch structure 20, which includes a substrate 207, a layer of anti-allergic gel 209 that can be in contact with the skin coated under the substrate, and a plurality of bottom electrodes (211a, 211b, 211c) disposed on the substrate 207 and exposed beyond the outer side of the gel layer 209, which are used to check whether the attachment of the piezoelectric patch 20 is completed, an insulating layer 213 disposed on the substrate 207 as a planarization layer, a piezoelectric material layer 201 attached to the insulating layer 213, metal leads 203 extend and connect with the adjacent circuit board 205 (the electrical connection 204 can be obtained by applying conductive glue, or button joints, etc.), a cover plate 215 and an encapsulant 217, where the encapsulant 217 is used to laminate-and-package the cover plate 215 and the substrate 207 as a protective layer by pressing or rolling process. The lower part of the figure is a front view of the piezoelectric patch structure 20 proposed by the present invention. The insulating layer 213, the substrate 207, and the gel layer 209 are stacked from bottom to top to form a substrate stack 220.

In one embodiment, the material of the above-mentioned substrate 207 can be glass, or plastics such as polyimide (PI), or polyethylene terephthalate (PET), etc., may also be textile.

In one embodiment, the encapsulant 217 is ethylene/vinyl acetate copolymer (EVA).

In one embodiment, the material of the cover plate 215 is glass or plastics such as polyimide (PI), or polyethylene terephthalate (PET), etc., may also be textile.

In one embodiment, the thickness of the piezoelectric patch structure 20 is less than 2000 μm, the thickness of the gel layer 209 is less than 700 μm; the thickness of the substrate 207 is less than 300 μm; the thickness of the insulating layer 213 is less than 50 μm; the thickness of the piezoelectric material layer 201 is less than 50 μm; the thickness of circuit board 205 is less than 200 μm; the thickness of encapsulation glue 217 is less than 300 μm.

In one embodiment, the above-mentioned piezoelectric sensor can also be replaced by an acceleration sensor, a gyroscope or other sensors.

Figure 3A:
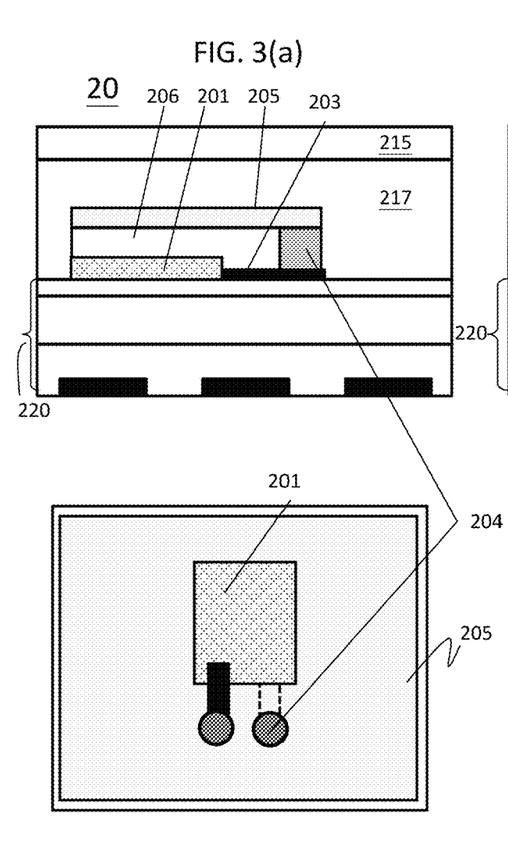
FIGS. 3(a)-3(c) respectively illustrate embodiments of different designs of piezoelectric patch structures.
Figure 3B:
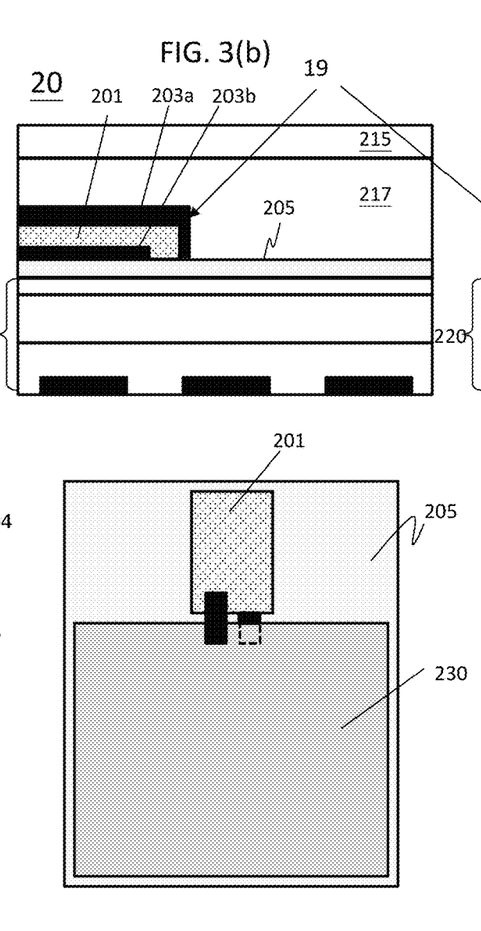
Figure 3C:
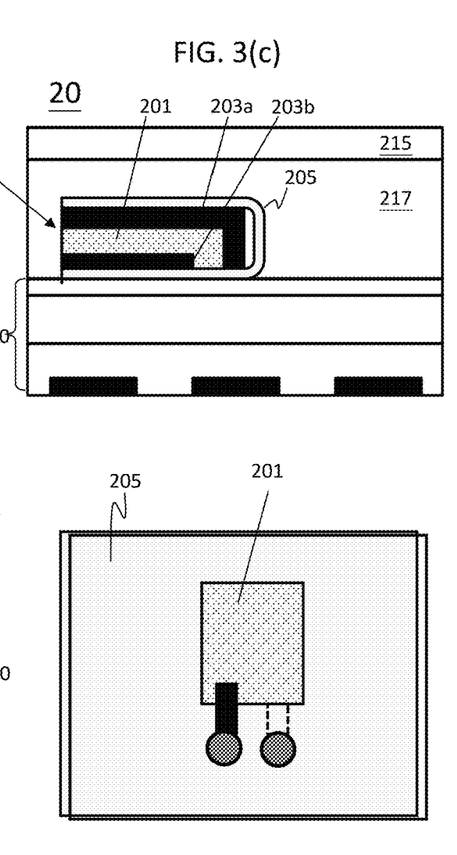

FIGS. 3(a)-3(c) respectively show different designs of the piezoelectric patch structure 20. In FIG. 3(a), the piezoelectric patch structure 20 is formed by placing the circuit board 205 above the piezoelectric material 201, the piezoelectric material layer 201 is attached on the insulating layer 213, the circuit board 205 is attached above the piezoelectric material 201 through the paste 206, and the electrical connection 204 between the circuit board 205 and the metal leads 203 plated on the piezoelectric material 201 is formed by means of conductive glue or button joints. FIG. 3(b) shows that the piezoelectric material 201 is directly attached to the circuit board 205, and the metal leads (203a, 203b) of the piezoelectric sensor structure 19 are electrically connected to a system circuit board 230. FIG. 3(c) shows that the piezoelectric material 201 is directly attached to the circuit board 205, and the circuit board 205 is a flexible circuit board that can be bent directly above the piezoelectric sensor structure 19.

Figure 4A:
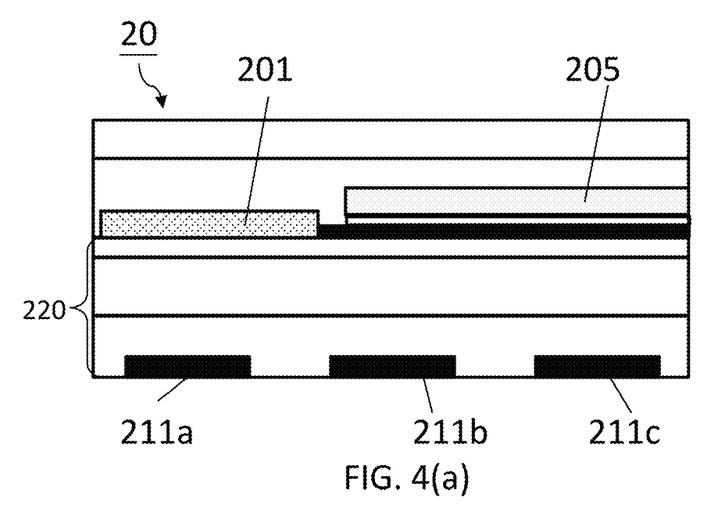
FIGS. 4(a)-(c) show the manner of the attachment test for the piezoelectric patch structure.
Figure 4B:
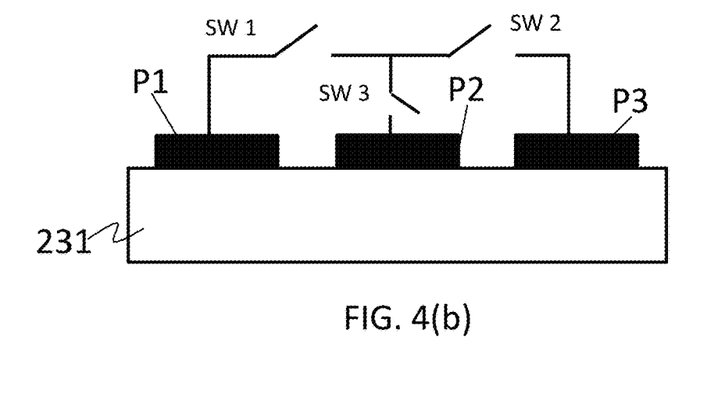
Figure 4C:
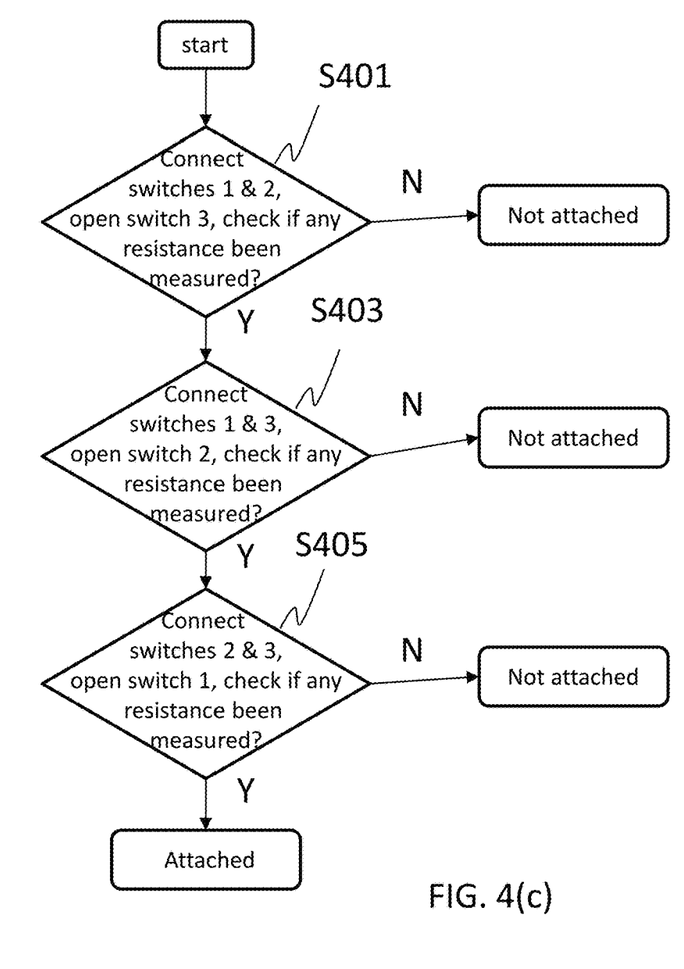

FIG. 4(a)-4(c) illustrates how to perform the attachment tests for the piezoelectric patch structure, take the piezoelectric patch structure shown in FIG. 4(a) as an example, its stacking structure has been illustrated in FIG. 2(b) and the details can be refer to the corresponding descriptions, the piezoelectric patch structure contains a plurality of electrodes (211a, 211b, 211c) bottom disposed on the substrate 207 and exposed below the outer side of the gel layer 209. The plurality of bottom electrodes (211a, 211b, 211c) can also be named as a first electrode P1, a second electrode P2 and a third electrode P2, accordingly, as shown in FIG. 4(b), a switch configuration circuit is designed between the plurality of bottom electrodes to test the attachment between the piezoelectric patch structure 20 and the skin resistance 231 of human. Where the above-mentioned switch configuration circuit is configured to connect the circuit loop between the first electrode P1 and the third electrode P3 in series with the first switch SW1 (switch 1) and the second switch SW2 (switch 2); the circuit loop between the first electrode P1 and the second electrode P2 is connected in series with the first switch SW1 (switch 1) and the third switch SW3 (switch 3); the circuit loop between the third electrode P3 and the second electrode P2 is connected in series with the second switch SW2 (switch 2) and the third switch SW3 (switch 3). When the above switch configuration circuit is set as shown in FIG. 4(b), the method of performing tests of attachment of the piezoelectric patch structure 20 is explained as follows. First, in step S401, connect the first switch SW1 (switch 1) and the second switch SW2 (switch 2), open the third switch SW3 (switch 3), check whether there is any resistance measured, if not, it is not completely attached between P1 and P3; if yes, go to step S403, connect the first switch SW1 (switch 1) and the third switch SW3 (switch 3), open the second switch SW2 (switch 2), check whether there is any resistance measured, if not, it is not completely attached between P1 and P2; if yes, go to step S405, connect the second switch SW2 (switch 2)) and the third switch SW3 (switch 3), open the first switch SW1 (switch 1), check whether there is any resistance measured, if not, it is not completely attached between P2 and P3, if yes, the attachment is completed.

Another embodiment of the heart sound capturing device 101 is a microphone composed of a capacitive sensor. The main composition of the microphone is a capacitive sensor, which uses an ultra-thin material as the diaphragm (for example, glass with 30 µm thickness), the diaphragm is plated with conductive material and sealed with the circuit board to form a resonance chamber. The design purpose of the heart sound capturing device is to capture changes of capacitance between the diaphragm and the circuit board causing by the emitted sound from the heartbeats to vibrate the diaphragm.

Utilizing traditional wearable capacitive sensor for sound sensing, due to environmental noise and other issues, its contact situation with human body must be confirmed. Therefore, the present invention proposes to place a pressure sensor on the soundproof ring of the capacitive sensor. This pressure sensor can include piezoelectric, capacitive, resistive and other related technologies, and the placement of the pressure sensor can be located between the soundproof ring and the circuit board, or under the circuit board. Basically, the pressure sensor can generate corresponding pressure signals according to the degree of pressed forces, so the pressure sensor can justify the degree of fitness between the wearable capacitive sensor and the user according to the sensed pressure signals.

Figure 5A:
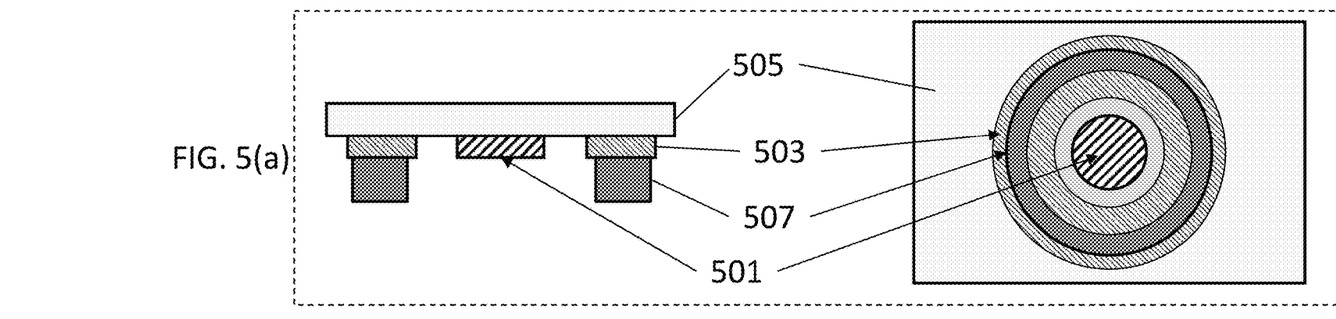
FIGS. 5(a)-(c) show various possible embodiments of pressure sensor configurations in capacitive sensors, respectively.
Figure 5B:
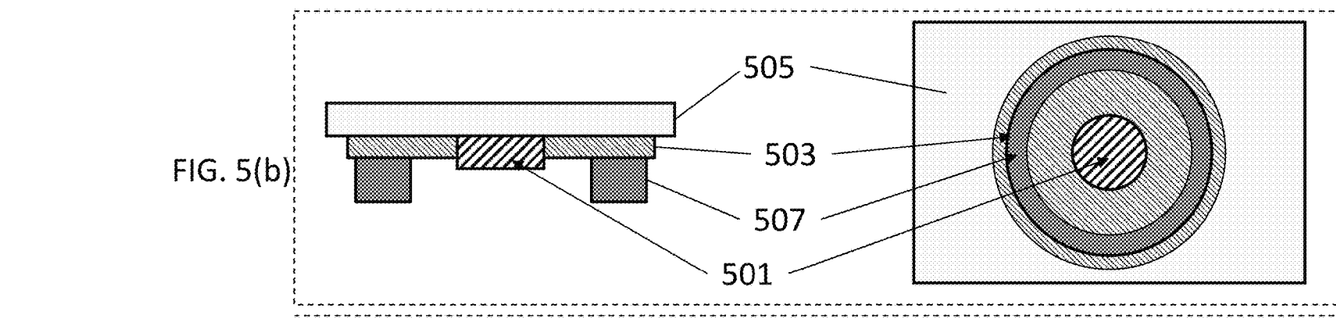
Figure 5C:
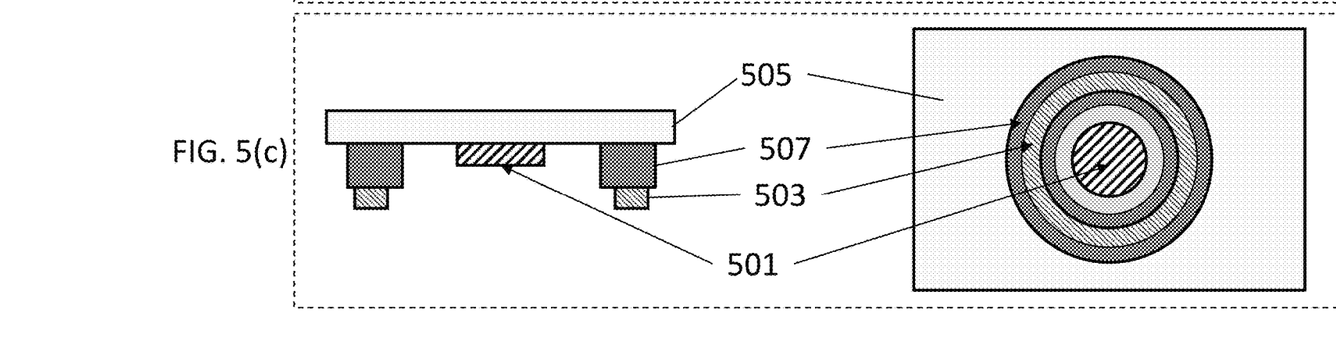

For the capacitive sensor proposed by the present invention, refer to FIGS. 5(a)-5(c), which respectively show several possible embodiments of the pressure sensor configuration, wherein the left of each figure is a side view and the right is a top view of the corresponding pressure sensor. One type of the pressure sensor configuration, please refers to FIGS. 5(a)-(b), in this type of configuration where the pressure sensor 503 is disposed between the circuit board 505 of the capacitive sensor 501 and the soundproof ring 507. The other type of the pressure sensor configurations, as shown in FIG. 5(c), the pressure sensor 503 is arranged below the soundproof ring 507.

Based on the above issues that the wearable capacitive sensor may face the technical obstacles, for example, poor response at low frequency and large environmental noise, the present invention proposes to integrate the piezoelectric sensor structure disclosed in FIGS. 3-4 as well as the wearable heart sound capturing device of the capacitive sensor disclosed in FIG. 5, the integrated wearable heart sound capturing device will be discussed in the following paragraphs.

Figure 6A:
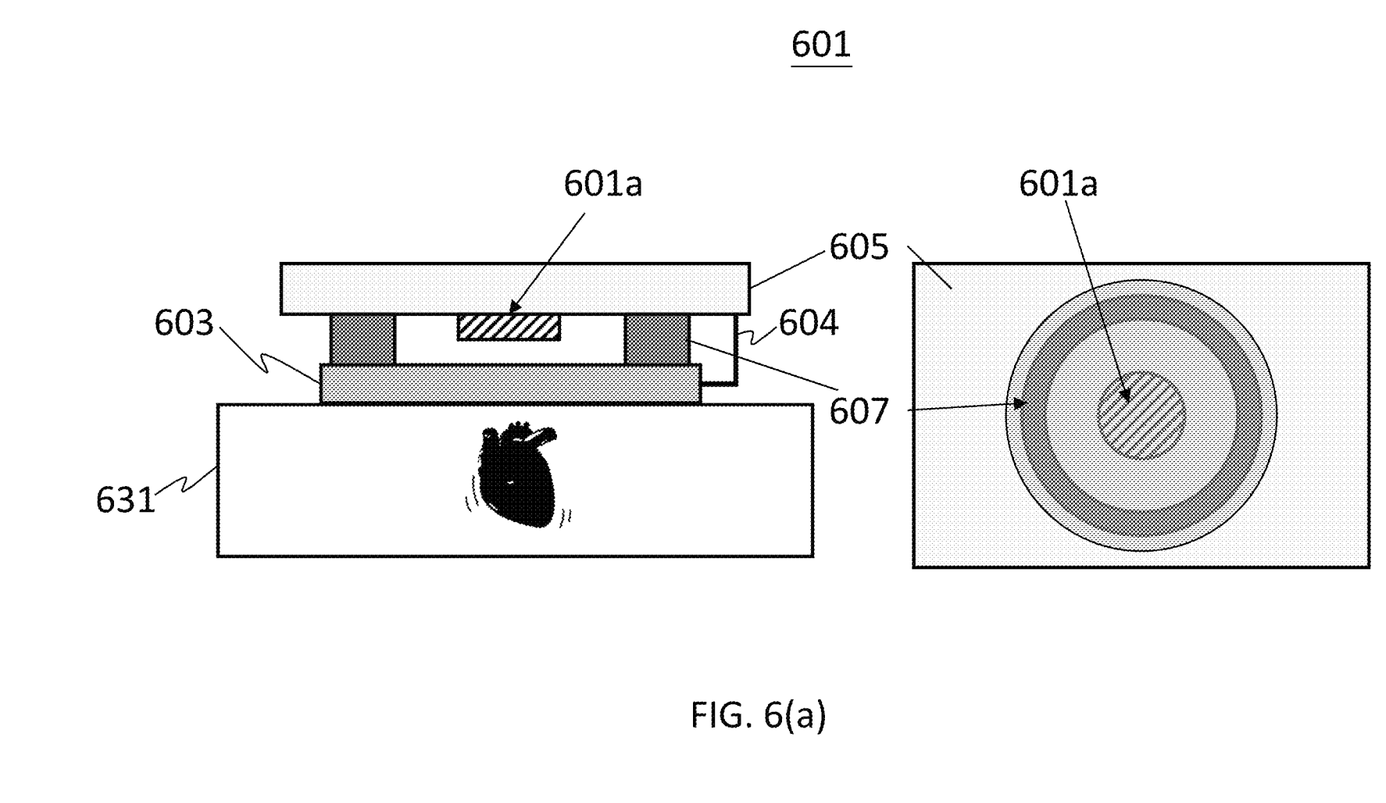
FIG. 6(a) shows an integrated wearable heart sound capturing device according to one embodiment of the present invention.

FIG. 6(a) shows an integrated wearable heart sound capturing device 601 according to an embodiment of the present invention, which includes a diaphragm 601a plated with a conductive material, a plastic frame (soundproof ring) 607 enclosed the diaphragm 601, a circuit board 605, and a piezoelectric sensor 603 disposed below the soundproof ring 607, where a resonance cavity formed by the soundproof ring 607 and the circuit board 605 together with the diaphragm 601a form a microphone structure. The piezoelectric sensor 603 contacted with human skin 631 is electrically connected to the circuit board 605 through a conduction wiring 604 for measuring voltage signals generated by vibrations. That is, the piezoelectric sensor 603 can be used as a diaphragm to assist the traditional capacitive sensor for improving its poor response to low-frequency signals, such as the third and fourth heart sounds with frequencies around 20 Hz.

In one embodiment, the piezoelectric sensor 603 may be formed on a flexible substrate (refer to FIG. 2) and fabricated in a patch form. Among them, the bottom of the flexible substrate is provided with a plurality of electrodes, which can be used to justify whether the attachment is completed.

In one embodiment, the integrated wearable heart sound capturing device 601 can be directly attached to the skin 631 above the user's heart position through a patch to measure the heart sound signals.

Figure 6B:
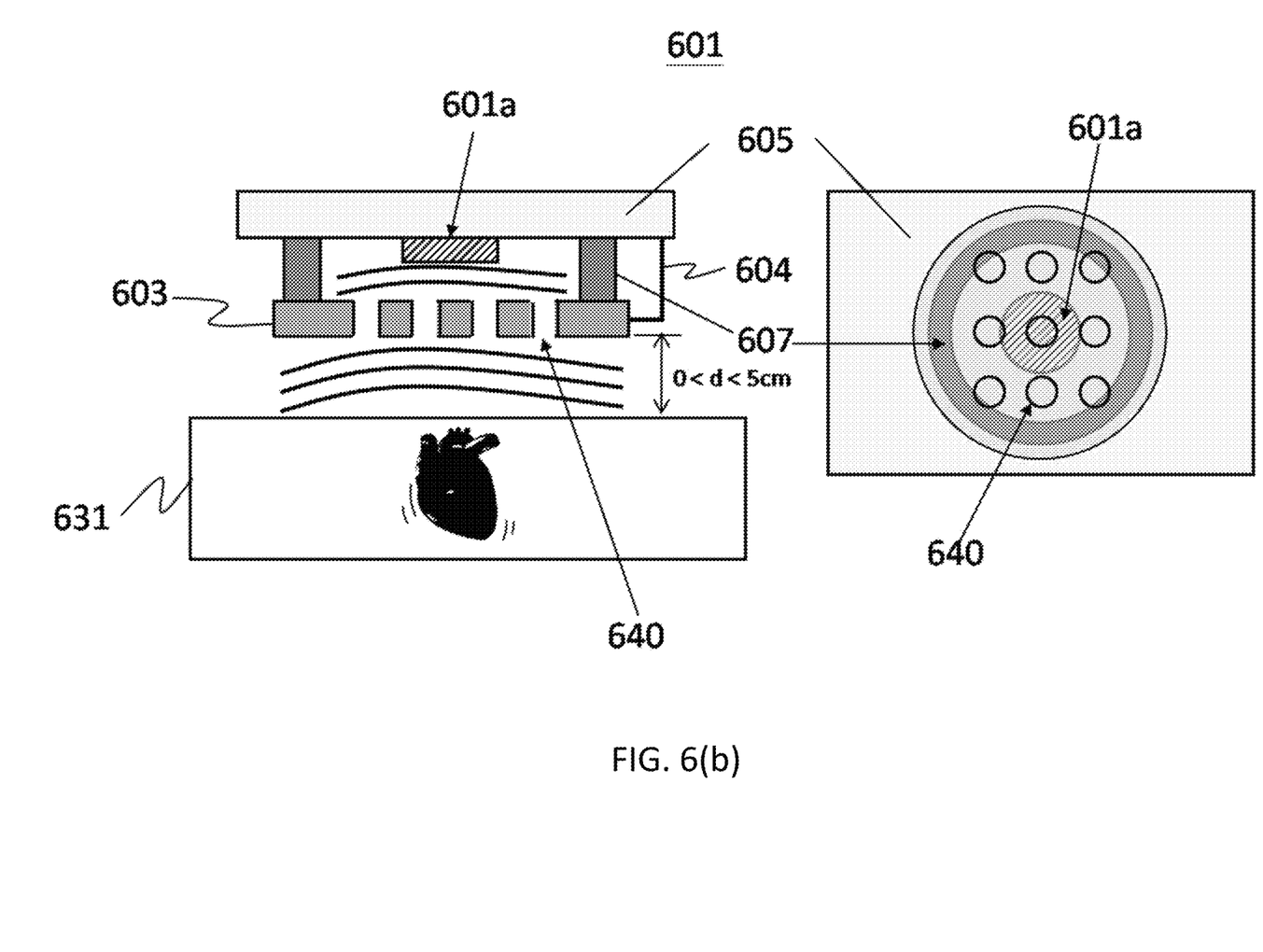
FIG. 6(b) shows an integrated wearable heart sound capturing device according to another embodiment of the present invention.

FIG. 6(b) shows an integrated wearable heart sound capturing device 601 according to another embodiment of the present invention, which includes a diaphragm 601a plated with conductive material, a plastic frame (soundproof ring) 607 enclosed the diaphragm 601a, a circuit board 605, and a piezoelectric sensor 603 with a plurality of holes 640 disposed below the soundproof ring 607, where a resonance cavity formed by the soundproof ring 607 and the circuit board 605 together with the diaphragm 601a form a microphone structure. The piezoelectric sensor 603 is electrically connected to the circuit board 605 through a conduction wiring 604 for measuring voltage signals generated by vibrations. This design allows sound to enter through the plurality of holes 640, and the integrated wearable heart sound capturing device 601 does not necessarily need to be in contact with the human body to measure heart sound signals.

In one embodiment, the size of the plurality of holes 640 disposed in the piezoelectric sensor 603 is in the range of 10 µm-1000 µm.

In one embodiment, the integrated wearable heart sound capturing device 601 with a plurality of holes in the piezoelectric sensor 603 can be operated by placing it in the proximity of human skin 631 within a distance d, wherein the distance d between the piezoelectric sensor 603 and the human skin 631 is in the range of 0<d<5 cm.

The design of the above-mentioned sensor is mainly used to receive signals of heart beating. The integrated wearable heart sound capturing device proposed by the present invention can receive the heartbeat signals from the capacitive sensor and the piezoelectric sensor respectively. In the integrated wearable heart sound capturing device, the circuit board includes electronic components such as several amplifiers, filters, power management systems, identification systems, Bluetooth, and processors.

Figure 7:
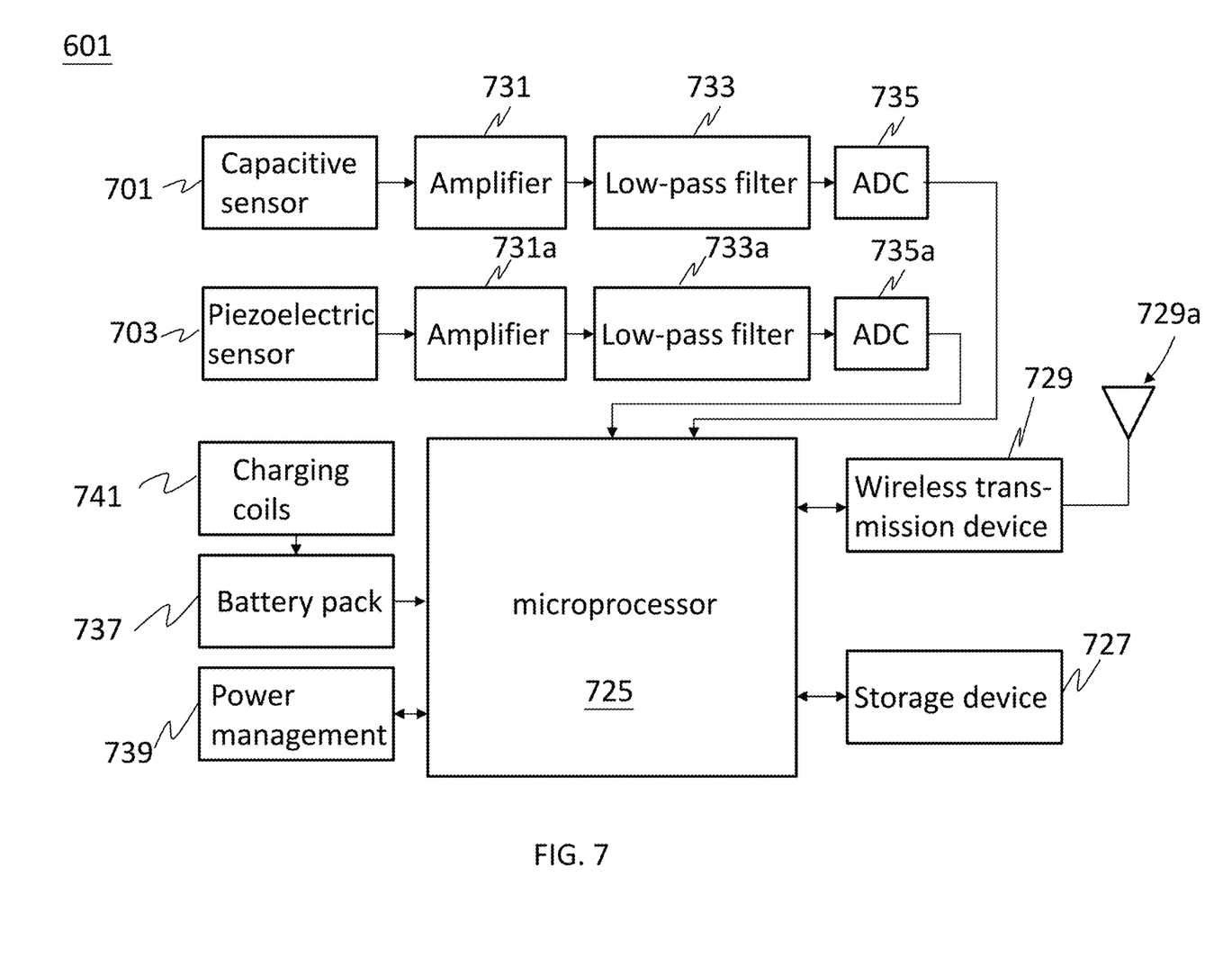
FIG. 7 shows a functional block diagram of a wearable heart sound capturing device according to one embodiment of the present invention.

FIG. 7 shows a functional block diagram of the wearable heart sound capturing device 601, which can obtain the heart sound signals from the human body through the capacitive sensor 701 and the piezoelectric sensor 703, respectively. The wearable heart sound capturing device 601 can receive and send data, execute software applications, which includes a microprocessor 725, a storage device 727, and a wireless transmission device 729.

Microprocessor 725 may be a microcontroller, a digital signal processor (DSP), an application specific integrated circuit (ASIC), a programmable logic circuit, or other digital data processing device that executes instructions to perform processing operations in accordance with the present invention. The microprocessor 725 can execute various application programs stored in the storage device, including executing firmware algorithms.

The storage device 727 may include read only memory (ROM), random access memory (RAM), electrically erasable programmable ROM (EEPROM), flash memory, or any memory commonly used in computers.

The wireless transmission device 729 is connected to an antenna 729a, which is configured to transmit output data and receive input data through a wireless communication channel. The wireless telecommunication channel may be a digital wireless telecommunication channel such as WiFi, Bluetooth, RFID, NFC, 3G/4G/5G or any other wireless communication interface will be announced in the near future.

The above-mentioned heart sound signals are individually obtained from the human body through the capacitive sensor 701 and the piezoelectric sensor 703, the received heart sound signals are respectively amplified by the first amplifier 731 and the second amplifiers 731a and then filtered by the first and second low-pass filter (733, 733a) to filter out noise. The amplified and filtered heart sound signals pass through the first and second analog-to-digital converters (ADC) (735, 735a) to convert analog signals into digital signals and then processed by the microprocessor 725 to obtain de-noising and stable heart sound signals. The microprocessor 725 can store the aforementioned de-noising and stable heart sound signals in the storage device through instructions or programs, or send these signals to the mobile device, such as smart phone, through the wireless transmission device 729 for further analysis.

The battery pack 737 provides power for the wearable heart sound capturing device 601, and can cooperate with the power management device 739 to optimize power usage. In addition, the battery pack 737 can also be wirelessly charged through charging coils 741.

In one embodiment, the microprocessor 725, storage device 727, wireless transmission device 729, amplifiers (731,731a), low-pass filters (733, 733a), analog-to-digital converters (ADC) (735, 735a), and the power management device 739 can be integrated into a single circuit assembly.

Figure 8:
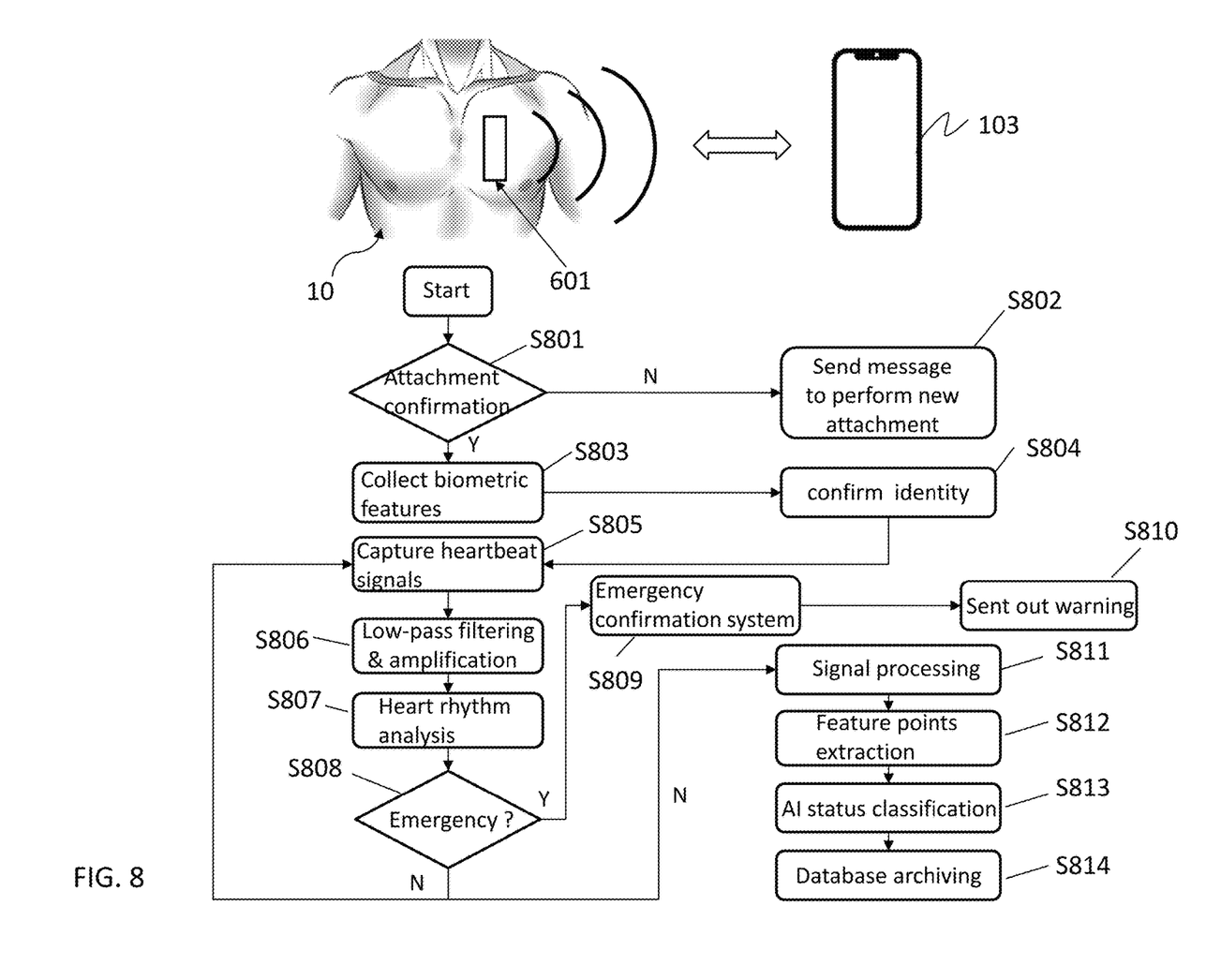
FIG. 8 shows a flowchart of establishing a wearable heart sound detection system according to one embodiment of the present invention.

According to FIGS. 2-7 and related embodiments, the present invention proposed to establish a wearable heart sound detection system as shown in FIG. 1, which is mainly divided into a sensor portion (wearable heart sound capture device) 601 and a device portion (smart phone or tablet computer, etc.) 103 to provide continuous monitoring of the heart condition, and can send alarms through the mobile device 103 to call for help in emergency situations. The execution steps of establishing the wearable heart sound detection system is shown in FIG. 8.

First, in step S801, confirming the attachment of the wearable heart sound capturing device 601 to a user's body 10, if the attachment is not completed, the mobile device 103 will continue to notify user to perform new attachment (step S802), the next step will be taken when the attachment is completed; next, in step S803, collecting biometric features of the user, for example ECG signals of the user, by the wearable heart sound capturing device 601; then, in step S804, use the collected biometric features to confirm the identity of the user; after confirming the identity by the mobile device 103, proceed to step S805, in this step, the heart sound capturing device 601 is used to capture the heartbeat signals of the user, including heart sound signal collection; next, in step S806, filtering and amplifying the heart sound signal by low-pass filter and amplifier of the heart sound capturing device 601; in step S807, perform preliminary heart rhythm analysis on the heart sound signals; after heart rhythm analysis, in step S808, first checking whether there exist emergency situations, if yes (such as heartbeat not been measured . . . ), immediately connect the mobile device 103 to compare with other sensors (step S809), if it is determined to be an emergency situation, immediately send out an alarm (or alarms) by the mobile device 103 (step S810); otherwise, sending out the heart sound signals to the mobile device 103 for detailed signal processing (step S811) and continue to collect the signal (step S805); after receiving the normal heart sound signals, the mobile device 103 performs signal processing, such as filtering, wavelet analysis, Fourier transform, etc., and extracts the heart sound signal feature points (step S812); next, in step S813, performing artificial intelligence (AI) comparison and status classification between the extracted feature points and the database with the previous stored data by the mobile device 103 to find out whether there are any abnormal signs; then, in step S814, the results of the above comparison and status classification are sent from the mobile device 103 to the database as references for subsequent comparisons, and are handed over to medical specialists for interpretation and providing medical-related advices.

In one embodiment, the above-mentioned database may be a cloud database arranged on a cloud server.

In one embodiment, the above-mentioned AI comparison and status classification are performed through the AI algorithm provided in the mobile device 103 to preliminarily classify the normal heart sound signals and the abnormal heart sound signals. The AI algorithm can include a series of steps: pre-filtering and normalizing the input heart sound signals, extracting time-domain and frequency-domain features, and adapting the convolutional neural networks (CNN) model to analysis and output classification results.

In one embodiment, the step of pre-filtering and normalization of the above-mentioned heart sound signals is performed in a software.

While various embodiments of the present invention have been described above, it should be understood that they have been presented by a way of example and not limitation. Numerous modifications and variations within the scope of the invention are possible. The present invention should only be defined in accordance with the following claims and their equivalents.

What is claimed is:

1. A wearable heart sound detection system, said system comprising:
   an acoustic sensing device for collecting heart sound signals of user's body, performing signal amplification, filtering, digitization on said collected heart sound signals, and outputting preprocessed heart sound signals;
   an external computing electronic device communicatively coupled to said acoustic sensing device for acquiring said preprocessed heart sound signals; and
   a cloud database communicatively coupled to said external computing electronic device;
   wherein said acoustic device includes a capacitive sound sensor, a piezoelectric sound sensor and a circuit assembly, said circuit assembly is respectively electrically connected with said capacitive sound sensor and said piezoelectric sound sensor;
   wherein said circuit assembly, said capacitive sound sensor and said piezoelectric sound sensor are integrated on a flexible substrate.

2. The wearable heart sound detection system of claim 1, wherein said circuit assembly at least includes:
   a plurality of amplifiers, a plurality of filters, a plurality of analog-to-digital converters, a microprocessor, a storage device, a wireless transmission device;
   output end of said capacitive sound sensor electrically connected to a first amplifier of said plurality of amplifiers, said first amplifier electrically connected to a first filter of said plurality of filters, said first filter electrically connected to a first analog-to-digital converter of said plurality of analog-to-digital converters, and said first analog-to-digital converter electrically connected to said microprocessor, wherein said first analog-to-digital converter outputs amplified, filtered and digitized first heart sound signals;
   output end of said piezoelectric sound sensor electrically connected to a second amplifier of said plurality of amplifiers, said second amplifier electrically connected to a second filter of said plurality of filters, said second filter electrically connected to a second analog-to-digital converter of said plurality of analog-to-digital converters, and said second analog-to-digital converter electrically connected to said microprocessor, wherein said second analog-to-digital converter outputs amplified, filtered and digitized second heart sound signals;
   said microprocessor receiving and processing said digitized first heart sound signals and said digitized second heart sound signals to obtain de-noising and stable preprocessed first heart sound signals and preprocessed second heart sound signals;
   wherein said microprocessor execute instructions to store the preprocessed first heart sound signals and the preprocessed second heart sound signals in said storage device electrically connected to said microprocessor, or to send the preprocessed first heart sound signals and the preprocessed second heart sound signals to said external computing electronic device via said wireless transmission device for further analysis.

3. The wearable heart sound detection system of claim 1, wherein said circuit assembly, said capacitive sound sensor and said piezoelectric sound sensor are arranged as follows:
   said capacitive sound sensor been disposed on a surface of said circuit assembly;
   a soundproof ring been arranged on said surface and enclosed to encapsulate said capacitive sound sensor and said circuit assembly to form a resonant cavity;
   said piezoelectric sound sensor been disposed on a side of said soundproof ring not in contact with said circuit assembly, wherein said piezoelectric sound sensor is attached to said user's skin near heart.

4. The wearable heart sound detection system of claim 3, wherein said piezoelectric sound sensor is further provided with a plurality of through holes, enabling that said heart sound signals can enter said resonant cavity of said capacitive sound sensor through said plurality of through holes.

5. The wearable heart sound detection system of claim 3, wherein said piezoelectric sound sensor is acted as a diaphragm to improve low-frequency sound signal response of said capacitive sound sensor.

6. The wearable heart sound detection system of claim 1, wherein said flexible substrate is made of polyimide (PI), polyethylene terephthalate (PET), or textile.

7. The wearable heart sound detection system of claim 1, further including following steps to establish said system:
   establishing attachment confirmation between said user's body and said acoustic sensing device;
   collecting said user's biometric features by said acoustic sensing device;
   identifying said user's identity by said collected biometric features;
   capturing said user's heartbeat signals including heart sound signals by said acoustic sensing device;
   filtering and amplifying said heart sound signals;
   performing heart rhythm analysis on said heart sound signals by said acoustic sensing device;
   checking whether emergency situations existed after said heart rhythm analysis being performed;
   sending out alarms by said external computing electronic device, if one of said emergency situations is justified, otherwise sending out said heart sound signals to said external computing electronic device for detailed signal processing and continuously capturing said user's heartbeat signals;
   extracting feature points of said heart sound signals by said external computing electronic device;
   performing artificial intelligence (AI) comparison and status classification between said extracted feature points and with previous stored data provided by said cloud database;
   archiving results of said AI comparison and status classification on said cloud database as references for subsequent comparisons and offering said results to interpret and provide medical-related advices by medical specialists.

8. The wearable heart sound detection system of claim 7, wherein said AI comparison and said status classification are performed by an AI algorithm installed on said external computing electronic device to preliminarily classify normal heart sound signals and abnormal heart sound signals.

9. The wearable heart sound detection system of claim 8, wherein said AI algorithm includes performing steps of:
   pre-filtering and normalizing said heart sound signals been input;
   extracting time-domain and frequency-domain features of said heart sound signals been input;
   outputting classification results by adopting convolutional neural networks (CNN) model.

10. The wearable heart sound detection system of claim 7, wherein said detailed signal processing includes performing filtering, wavelet analysis, and Fourier transform over said heart sound signals.

11. A wearable heart sound detection system, said system comprising:
- an acoustic sensing device for collecting heart sound signals of user's body, performing signal amplification, filtering, digitization on said collected heart sound signals, and outputting preprocessed heart sound signals;
- an external computing electronic device communicatively coupled to said acoustic sensing device for acquiring said preprocessed heart sound signals; and
- a cloud database communicatively coupled to said external computing electronic device;
- wherein said acoustic device includes a capacitive sound sensor, a piezoelectric sound sensor and a circuit assembly, said circuit assembly is respectively electrically connected with said capacitive sound sensor and said piezoelectric sound sensor;
- wherein said circuit assembly, said capacitive sound sensor and said piezoelectric sound sensor are arranged as follows:
- said capacitive sound sensor been disposed on a surface of said circuit assembly;
- a soundproof ring been arranged on said surface and enclosed to encapsulate said capacitive sound sensor and said circuit assembly to form a resonant cavity;
- said piezoelectric sound sensor been disposed on a side of said soundproof ring not in contact with said circuit assembly, wherein said piezoelectric sound sensor is attached to said user's skin near heart
- wherein said circuit assembly, said capacitive sound sensor and said piezoelectric sound sensor are integrated on a flexible substrate.

12. The wearable heart sound detection system of claim 11, wherein said circuit assembly at least includes:
- a plurality of amplifiers, a plurality of filters, a plurality of analog-to-digital converters, a microprocessor, a storage device, a wireless transmission device;
- output end of said capacitive sound sensor electrically connected to a first amplifier of said plurality of amplifiers, said first amplifier electrically connected to a first filter of said plurality of filters, said first filter electrically connected to a first analog-to-digital converter of said plurality of analog-to-digital converters, and said first analog-to-digital converter electrically connected to said microprocessor, wherein said first analog-to-digital converter outputs amplified, filtered and digitized first heart sound signals;
- output end of said piezoelectric sound sensor electrically connected to a second amplifier of said plurality of amplifiers, said second amplifier electrically connected to a second filter of said plurality of filters, said second filter electrically connected to a second analog-to-digital converter of said plurality of analog-to-digital converters, and said second analog-to-digital converter electrically connected to said microprocessor, wherein said second analog-to-digital converter outputs amplified, filtered and digitized second heart sound signals;
- said microprocessor receiving and processing said digitized first heart sound signals and said digitized second heart sound signals to obtain de-noising and stable preprocessed first heart sound signals and preprocessed second heart sound signals;
- wherein said microprocessor execute instructions to store the preprocessed first heart sound signals and the preprocessed second heart sound signals in said storage device electrically connected to said microprocessor, or to send the preprocessed first heart sound signals and the preprocessed second heart sound signals to said external computing electronic device via said wireless transmission device for further analysis.

13. The wearable heart sound detection system of claim 11, wherein said piezoelectric sound sensor is further provided with a plurality of through holes, enabling that said heart sound signals can enter said resonant cavity of said capacitive sound sensor through said plurality of through holes.

14. The wearable heart sound detection system of claim 11, wherein said piezoelectric sound sensor is acted as a diaphragm to improve low-frequency sound signal response of said capacitive sound sensor.

15. The wearable heart sound detection system of claim 11, wherein said flexible substrate is made of polyimide (PI), polyethylene terephthalate (PET), or textile.

16. The wearable heart sound detection system of claim 13, wherein size of said plurality of through holes is ranging between 10 μm-1000 μm.

17. The wearable heart sound detection system of claim 13, wherein said acoustic sensing device is capable of collecting said heart sound signals of said user's body while been disposed within a distance without need to contact with said user's body.

18. The wearable heart sound detection system of claim 17, wherein said distance is ranging between 0 cm-5 cm.

* * * * *